United States Patent [19]

Harris et al.

[11] Patent Number: 4,933,407

[45] Date of Patent: Jun. 12, 1990

[54] FUNCTIONALIZED OXACALIXARENES, THEIR PREPARATION AND USE IN INSTANT ADHESIVE COMPOSITIONS

[75] Inventors: Stephen J. Harris; Maureen G. MacManus, both of Dublin, Ireland

[73] Assignee: Loctite (Ireland) Ltd., Dublin, Ireland

[21] Appl. No.: 383,782

[22] Filed: Jul. 21, 1989

Related U.S. Application Data

[62] Division of Ser. No. 145,993, Jan. 20, 1988, Pat. No. 4,855,461.

[30] Foreign Application Priority Data

Jan. 21, 1987 [IE] Ireland .................................. 153/87

[51] Int. Cl.$^5$ .................. C07D 313/00; C07D 321/00; C07D 323/00; C08F 2/44
[52] U.S. Cl. .................................... 526/208; 526/204; 526/209; 549/348
[58] Field of Search ........................ 526/204, 208, 209

[56] References Cited

U.S. PATENT DOCUMENTS 4,098,717  7/1978  Burkis ................................. 252/331
4,622,414  11/1986  McKervey .............................. 560/61

*Primary Examiner*—Joseph L. Schofer
*Assistant Examiner*—Thomas McDonald, Jr.
*Attorney, Agent, or Firm*—Edward K. Welch, II; Eugene F. Miller

[57] ABSTRACT

Oxacalixarenes of general formula I:

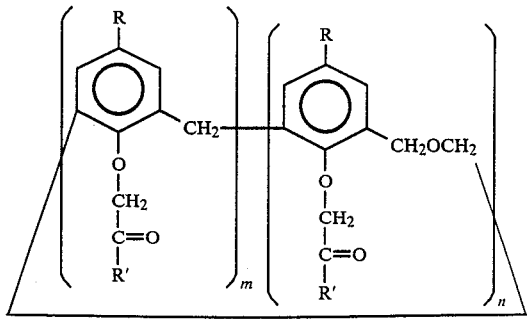

wherein
m=0–7 and n=1–8 with the proviso that m+n≦8;
R is hydrogen, halogen, or hydrocarbyl, aryl, hydrocarbylaryl or a substituted derivative thereof, and R may be the same or different on each aryl group; and
R' is hydrocarbyl, aryl, hydrocarbylaryl, hydrocarbyloxy, aryloxy or hydrocarbylaryloxy or a substituted derivative thereof.

The invention also provides a method of preparing oxacalixarenes of formula I, and cyanoacrylate adhesive compositions including as accelerator an oxacalixarene of formula I.

11 Claims, No Drawings

FUNCTIONALIZED OXACALIXARENES, THEIR PREPARATION AND USE IN INSTANT ADHESIVE COMPOSITIONS

This is a divisional of copending application Ser. No. 07/145,993 filed on Jan. 20, 1988 now U.S. Pat. No. 4,855,461.

BACKGROUND OF THE INVENTION

1. Field of the Invention

The present invention relates to etherified oxacalixarenes which are useful for promoting adhesion of cyanoacrylate-based compositions to porous or deactivating surfaces, to a process for their preparation and to adhesive compositions comprising them.

2. Description of the Related Art

Various accelerators have been proposed for improving the curing time of cyanoacrylate-based adhesives on wood, paper or substrates with porous or deactivating surfaces. In general, these adhesive compositions require an accelerator which sequesters alkali metal cations. U.S. Pat. No. 4,171,416 suggests the use of crown ethers, which are macrocyclic molecules capable of complexing with a metallic ion. However, these compounds are highly toxic and therefore unsafe to use.

In U.S. Pat. No. 4,170,585, there are described cyanoacrylate compositions in which certain polyethylene glycols or poly(ethyleneoxy)-functional surfactants act as wood bonding accelerators. Such compounds, however, have the reported disadvantage that they tend to contain water and other difficult to remove substances which spontaneously initiate polymerization of the cyanoacrylate monomer.

U.S. Pat. No. 4,377,490 discloses mixtures of aromatic and aliphatic polyols and polyethers said to improve initial strength of cyanoacrylate wood bonding products.

U.S. Pat. No. 4,386,193 discloses certain 3 or 4 arm polyol podand compounds as alternatives to crown-ether accelerators.

Japan Kokai Tokkyo Koho 82-70171, suggests the use of certain polyorganosiloxane compounds which include polyether substituents as additives for wood bonding cyanoacrylate compositions. Chem. Abstracts, 97 145913n reports the use of a hydroxy-terminated poly(dimethylsiloxane) in fast bonding cyanoacrylate compositions.

DE-OS No. 3,006,071 discloses certain furan derivatives as co-accelerators with crown ethers in cyanoacrylate compositions.

U.S. Pat. No. 4,556,700 Harris et al describes the use of certain calixarene compounds as accelerators in cyanoacrylate compositions. Irish patent application No. 819/86 Loctite (Ireland) Limited describes further calixarene compounds including polymer-bound calixarene compounds which are also useful for this purpose.

SUMMARY OF THE INVENTION

The present invention provides novel oxacalixarenes of general formula I:

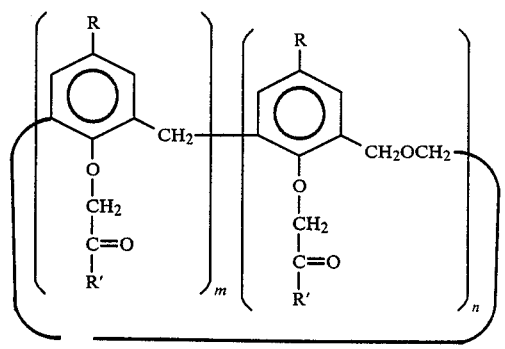

wherein $m=0-7$ and $n=1-8$ with the proviso that $m+n \leq 8$;

R is hydrogen, halogen, or hydrocarbyl, aryl, hydrocarbylaryl or a substituted derivative thereof, and R may be the same or different on each aryl group; and R' is hydrocarbyl, aryl, hydrocarbylaryl, hydrocarbyloxy, aryloxy or hydrocarbylaryloxy or substituted derivative thereof.

The methyl and ether bridges may or may not alternate within the oxacalixarene molecule.

Preferred etherified oxacalixarenes of formula I are:

(i) an oxacalix-4-arene which has the formula:

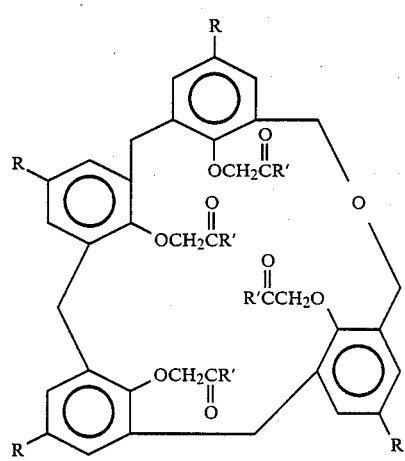

(ii) a dioxacalix-4-arene of formula:

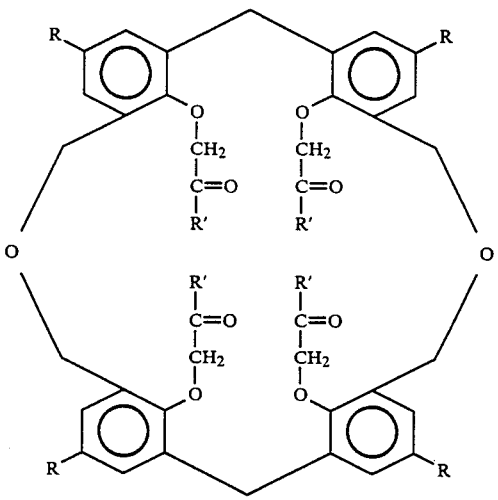

and (iii) a trioxacalix-3-arene of formula:

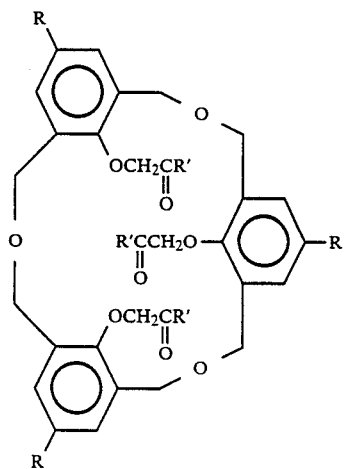

wherein R and R' are as defined above.

In the above compounds, the hydrocarbyl groups shall preferably contain from 1 to 10 carbon atoms, more preferably from 1 to 5 carbon atoms and the aryl and hydrocarbylaryl groups shall preferably have from 6 to 20 carbon atoms, more preferably from 6 to 10 carbon atoms. Hydrocarbyl groups are preferred, especially alkyl or alkenyl groups. A substituted derivative of the foregoing may suitably be substituted with one or more halo or oxo groups or interrupted by one or more oxa groups. Halogen may be chlorine, bromine, fluorine or iodine.

The oxacalixarenes of formula I are useful as adhesion promoting accelerators in alpha-cyanoacrylate compositions for bonding wood or other de-activating surfaces such as paper, leather, ceramic, plastics and metals with chromate-treated or acidic oxide surfaces. The inventive compositions are standard cyanoacrylate adhesive formulations to which have been added, as accelerators, calixarene compounds as defined above which are stable to cyanoacrylate monomers. The calixarene compounds are employed in amounts conventional for cyanoacrylate accelerators, preferably at levels between about 0.1% and 2% by weight of the composition.

The a-cyanoacrylate-type adhesive composition of this invention as described above contains an a-cyanoacrylate monomer of the formula:

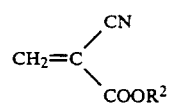

wherein $R^2$ represents a straight chain or branched chain alkyl group having 1 to 12 carbon atoms (which may be substituted with a substituent such as a halogen atom or an alkoxy group), a straight chain or branched chain alkenyl group having 2 to 12 carbon atoms, straight chain or branched chain alkynyl group having 2 to 12 carbon atoms, a cycloalkyl group, an aralkyl group or any aryl group. Specific examples of the groups for $R^2$ are a methyl group, an ethyl group, an n-propyl group, an isopropyl group, an n-butyl group, an isobutyl group, a pentyl group, a hexyl group, an allyl group, a methallyl group, a crotyl group, a propargyl group, a cyclohexyl group, a benzyl group, a phenyl group, a cresyl group, a 2-chloroethyl group, a 3-chloropropyl group, a 2-chlorobutyl group, a trifluoroethyl group, a 2-methoxyethyl group, a 3-methoxybutyl group and a 2-ethoxyethyl group. Ethyl cyanoacrylate is the preferred monomer for use in the inventive compositions.

A single a-cyanoacrylate monomer or a mixture of two or more of these a-cyanoacrylate monomers can be used. Generally, the above a-cyanoacrylate monomer alone is not sufficient as an adhesive, and the components set forth below are sometimes added:

(1) an anionic polymerization inhibitor
(2) a radical polymerization inhibitor
(3) a thickener
(4) special additives such as plasticizers and heat stabilizers
(5) perfumes, dyes, pigments, etc.

A suitable amount of the a-cyanoacrylate monomer present in the adhesive composition is about 80 to 99.9% by weight, preferably 90 to 99.9% by weight, based on the total weight of the adhesive composition.

An anionic polymerization inhibitor is added to the a-cyanoacrylate-type adhesive composition, e.g., in an amount of about 1 to 1000 ppm based on the total weight of the adhesive composition, to increase the stability of the adhesive composition during storage, and examples of known inhibitors are sulfur dioxide, aromatic sulfonic acids, aliphatic sulfonic acids, sultones, and carbon dioxide.

Suitable examples of radical polymerization inhibitors include, for example, hydroquinone and hydroquinone monomethyl ether. A radical polymerization inhibitor is added, e.g., in amount of about 1 to 5000 ppm based on the total weight of the adhesive composition, for the purpose of capturing radicals which are formed by light during storage.

A thickener is added to increase the viscosity of the a-cyanoacrylate-type adhesive composition. The a-cyanoacrylate monomer generally has a low viscosity of about several centipoises and, therefore, the adhesive penetrates into porous materials such as wood and leather or adherends having a rough surface. Thus, good adhesion strengths are difficult to obtain. Various polymers can be used as thickeners, and examples include poly(methyl methacrylate), methacrylate-type copolymers; acrylic rubbers, cellulose derivatives, polyvinyl acetate and poly(a-cyanoacrylate). A suitable amount of thickener is generally about 20% by weight or less based on the total weight of the adhesive composition.

As disclosed in the copending application of Alan Litke, Ser. No. 528,275, filed Aug. 31, 1983, now U.S. Pat. No. 4,477,607, certain fumed silica fillers treated with polydialkylsiloxanes or trialkylsilanes may also be usefully employed as cyanoacrylate thickeners.

The plasticizers, perfumes, dyes, pigments, etc., may be added depending on use purposes in amounts which do not adversely affect the stability of the a-cyanoacrylate monomer. The use of such additives is within the skill of those practicing in the cyanoacrylate adhesive art and need not be detailed herein.

Oxacalixarene compounds may be readily synthesised by methods described in C. D. Gutsche, B. Dhawan, K. H. No & R. Muthukrishnan, J. Am. Chem. Soc. 103 p3782 (1981); B. Dhawan & C. D. Gutsche, J. Org. Chem. 48 p1536 (1983) and U.S. Pat. No. 4,098,717, R. Buriks, A. R. Fauke & F. E. Mange; the appropriate disclosures of all of which are incorporated herein by reference.

The present invention also relates to a method of producing etherified oxacalixarenes of formula I wherein a phenolic oxacalixarene is reacted with a halomethylketone or a haloalkyl acetate. Potassium iodide may be added to accelerate etherification.

The present invention also relates to cyanoacrylate adhesive compositions including as accelerator an oxacalixarene of formula I:

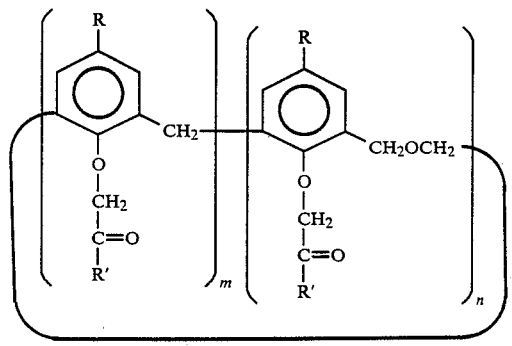

wherein m, n, R and R' are as defined above.

Preferably the etherified oxacalixarene comprises from 0.1 to 5% by weight of the total adhesive composition.

DESCRIPTION OF THE PREFERRED EMBODIMENTS

The following Examples serve to illustrate the invention.

EXAMPLE 1

Preparation: The tetraethyl acetate of 7,13,19,25-tetra-tert-butyl-27,28,29,30-tetrahydroxy-2,3-dihomo-3-oxacalix-4-arene.

7,13,19,25-tetra-tert-butyl 27,28,29,30-tetrahydroxy-2,3-dihomo-3-oxacalix-4-arene was prepared following the method of C. D. GUTSCHE, B. DHAWAN, K. H. No, & R. Muthukrishnan, J. Am. Chem. Soc. 103 p 3782 1981 from p-tert-butylphenol paraformaldehyde and aqueous 5N potassium hydroxide in refluxing xylene.

To 3.2 g of this compound (0.0047 mole) in 25 ml analar acetone was added 6.6 g (0.031 mole) ethyl bromoacetate and 4.2 g (0.030 mole) anhydrous potassium carbonate and the entire was refluxed under dry nitrogen with stirring for 120 hours. After this time all volatiles were removed including the excess ethyl bromoacetate under reduced pressure to give a buff coloured solid which was dissolved in 20 ml dichloromethane which was washed 3 times with 20 ml 10% aqueous $H_2SO_4$ and twice with 20 mls water. The separated dichloromethane layer was then dried over dried magnesium sulphate and volatiles were removed to give 4.0 g of product as a pale buff solid of yield 83%, which was chromatographed on acid-washed alumina and dichloromethane as eluent to give, following removal of volatiles, colourless solid tetraethyl acetate of 7,13,19,25-tetra-tert-butyl-27,28,29,30-tetrahydroxy-2,3-dihomo-3-oxacalix-4-arene m.pt. 63°–64° C., characterised by infra-red spectroscopy and elemental analysis.

I.R. Spectroscopy results: $\nu 1765$ (S) cm$^{-1}$ C=0.

Elemental analysis results (Calculated for $C_{61}H_{82}O_{13}$: C=71.59, H=8.08, O=20.34; Found: C=71.45, H=7.87, O=20.20).

EXAMPLE 2

Preparation: Tetraethyl acetate of 7,13,21,27-tetra-tert-butyl-29,30,31,32-tetrahydroxy-2,3,16,17-tetrahomo-3,17-dioxacalix-4-arene.

7,13,21,27-tetra-tert-butyl-29,30,31,32-tetrahydroxy-2,3,16,17-tetrahomo-3,17-dioxacalix-4-arene was prepared by the thermally induced dehydration of 3-[3-hydroxymethyl)-5-tert-butylsalicyl]-5-tert-butyl-2-hydroxybenzyl alcohol, itself prepared from p-tert-butylphenol, formaldehyde and aqueous NaOH at 50° C. following the procedure of B. DHAWAN and C. D. GUTSCHE J. Org. Chem. 48 (9) p. 1536 1983. To 0.5 g (0.0007 mole) 7,13,21,27-tetra-tert-butyl-29,30,31,32-tetrahydroxy-2,3,16,17-tetrahomo-3,17-dioxacalix-4-arene was added to 1.02 g (0.006 mole) ethyl bromoacetate and 0.65 g (0.0047 mole) anhydrous potassium carbonate and 10 mls analar acetone and the entire was refluxed under nitrogen with stirring for 120 hours. After this time all volatiles were removed including the excess ethyl bromoacetate under reduced pressure to give a buff-coloured sticky solid which was dissolved in 5 ml dichloromethane which was then washed 3 times with 5 ml 10% aqueous $H_2SO_4$ and then twice with 5 ml water. The separated dichloromethane was then dried over dried magnesium sulphate following which volatiles were removed to give 0.62 g product as a buff coloured solid of yield 74%. This solid was chromatographed on acid-washed alumina using dichloromethane as eluent to give the tetraethyl acetate of 7,13,21,27-tert-butyl-29,30,31,32-tetrahydroxy-2,3,16,17-tetrahomo-3,17-dioxacalix-4-arene as a colourless solid, m.pt. 211°–212° C. which was characterised by infra red spectroscopy and elemental analysis.

I.R. Spectroscopy results: $\nu 1760$(S)cm$^{-1}$ C=0.

Elemental Analysis: (Calculated for $C_{62}H_{84}O_{14}$: C=70.69, H=8.04, O=21.27; Found C=70.91, H=8.21, O=20.90).

EXAMPLE 3

Preparation: Triethyl acetate of 7,15,23-Tri-tert-butyl-2,3,10,11,18,19-hexahomo-3,11,19-trioxacalix-3-arene.

7,15,23-Tri-tert-butyl-2,3,10,11,18,19-hexahomo-3,11,19-trioxacalix-3-arene was prepared by the thermally induced dehydration of 2,6-bis (hydroxymethyl)-4-tert-butylphenol (itself prepared from p-t-butyl-phenol, aqueous NaOH and formaldehyde solution, following U.S. Pat. No. 4,098,717, Jul. 1978, by R. BURIKS, A. FAUKE and F. MANGE of Petrolite Corporation) following the method of B. DHAWAN and C. D. GUTSCHE in J. Org. Chem. 48(9) p.1536 1983. 0.9 g (0.00117 mole) of this compound was added to 1.17 g (0.0070 mole) ethyl bromoacetate and 0.72 (0.00 52 mole) anhydrous potassium carbonate and 10 mls analar acetone and the reaction mixture was refluxed with stirring under nitrogen for 120 hours. After cooling the reaction mixture was filtered and volatiles were removed from the filtrate under reduced pressure to give a pale yellow heavy oil which was taken up in 10 mls dichloromethane which was twice washed with 10 mls 5% aqueous $H_2SO_4$ and twice with 10 mls water. The dichloromethane layer was then dried with dried $MgSO_4$ and filtered and all volatiles were removed from the filtrate to give a pale yellow solid of product yield=1.23 g (94%), which was chromatographed on acid-washed alumina using dichloromethane as eluent to give the pure product as a colourless solid with a very sharp melting point m.pt. 45.5° C. confirmed as being the fully etherified tri(ethyl acetate) derivative of 7,15,23-Tri-tert-butyl-2,3,10,11,18,19-hexahomo-3,11,19-trioxacalix-3-arene by elemental and infra-red analysis.

I.R. Spectroscopy results: $\nu 1750$ (S)cm$^{-1}$ C=O.

Elemental Analysis: (Calculated for $C_{48}H_{66}O_{12}$: C=69.04, H=7.97, O=22.99; Found: C=67.66, H=7.96, O=22.16)

EXAMPLE 4

Ethyl cyanoacrylate stabilized with 10 ppm $BF_3$ was used as a base adhesive formulation. The additives shown below were dissolved in the base adhesive at the indicated level and fixture times on copy paper and white deal were determined. The results below demonstrate the good accelerative activity for these compounds.

| Additive | Amount | Fixture Time Copy Paper | White Deal |
|---|---|---|---|
| 0 | 0 | 60 seconds | 4–5 minutes |
| Example 1 | 1% | 5–10 seconds | 5–10 seconds |
| Example 2 | 1% | 15 seconds | 5–15 seconds |
| Example 3 | 1% | 30–40 seconds | 5 seconds |

We claim:

1. An improved cyanoacrylate adhesive composition comprising at least one cyanoacrylate monomer and an accelerator, in a conventional amount, wherein the improvement comprises including as the accelerator an oxacalixarene of the general formula

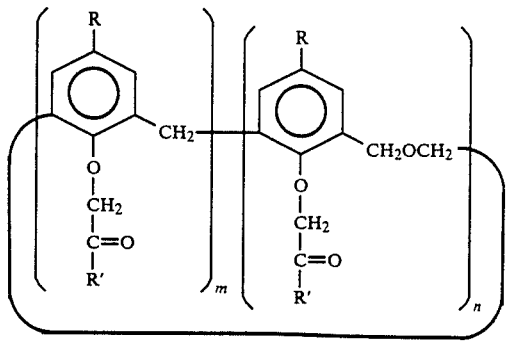

wherein m=0–7 and n=1–8 with the proviso that m+n≦8;

R is hydrogen, halogen, or hydrocarbyl, which may be substituted by one or more halo or oxo groups or interrupted by one or more oxa groups, and R may be the same or different on each aryl group; and $R^1$ is hydrocarbyl, which may be substituted by one or more halo or oxo groups or interrupted by one or more oxa groups, or hydrocarbyloxy, which may be substituted by one or more halo or oxo groups or interrupted by one or more oxa groups.

2. The cyanoacrylate adhesive composition of claim 1 wherein the oxacalixarene comprises from 0.1 to 5% by weight of the total adhesive composition.

3. The cyanoacrylate composition of claim 2 wherein hydrocarbyl refers to an alkyl or alkenyl group having from 1 to 10 carbon atoms.

4. The cyanoacrylate composition of claim 2 wherein hydrocarbyl refers to an alkyl or alkenyl group having from 1 to 5 carbon atoms.

5. The cyanoacrylate composition of claim 1 wherein halogen is chlorine, bromide or iodine.

6. The cyanoacrylate composition of claim 1 wherein the oxacalixarene is an oxacalix-4-arene having the formula

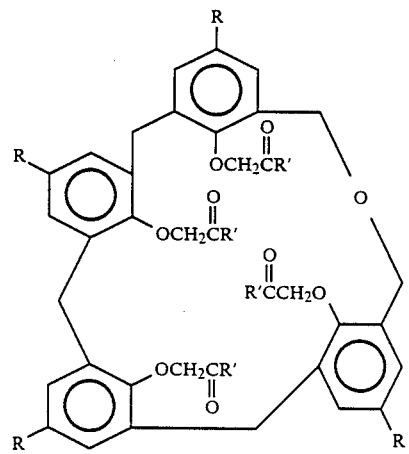

wherein R and $R^1$ are as defined in claim 1.

7. The cyanoacrylate composition of claim 1 wherein the oxacalixarene is a dioxacalix-4-arene of the formula

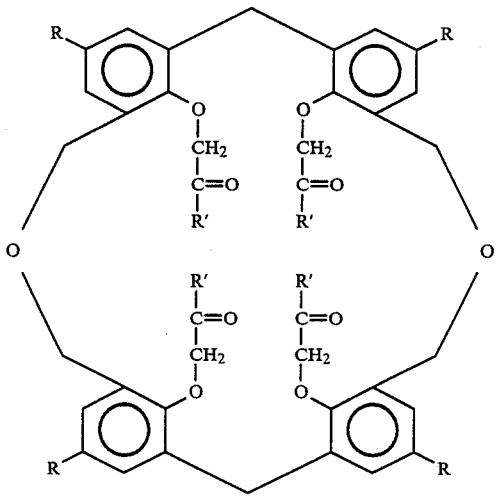

wherein R and R¹ are as defined in claim 1.

8. The cyanoacrylate composition of claim 1 wherein the oxacalixarene is a trioxacalix-3-arene of the formula

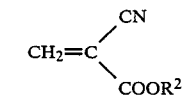

wherein R and R¹ are as defined in claim 1.

9. The cyanoacrylate composition of claim 1 wherein the cyanoacrylate monomer or monomer mixture is comprised of one or more monomers of the formula $$CH_2=C\begin{matrix}CN\\COOR^2\end{matrix}$$

wherein $R^2$ represents a substituted or unsubstituted straight chain or branched chain alkyl group having 1 to 12 carbon atoms, a straight chain or branched chain alkenyl group having 2 to 12 carbon atoms, a straight chain or branched chain alkynyl group having 2 to 12 carbon atoms, a cycloalkyl group, an aralkyl group or an aryl group.

10. The cyanoacrylate composition of claim 1 further comprising an anionic polymerization inhibitor and a free radical polymerization inhibitor.

11. The cyanoacrylate composition of claim 1 wherein the cyanoacrylate monomer comprises from about 80 to 99.9% by weight of the total adhesive composition.

* * * * *